United States Patent [19]

Barbič

[11] Patent Number: 5,765,764
[45] Date of Patent: Jun. 16, 1998

[54] METHOD AND APPARATUS FOR CONTROLLING THE GRINDING OF MINERAL RAW MATERIALS

[76] Inventor: Lenart Barbič, Kosmerice 7a, Most na Soči, Slovenia, 5216

[21] Appl. No.: 716,238

[22] PCT Filed: Mar. 20, 1995

[86] PCT No.: PCT/SI95/00006

§ 371 Date: Sep. 20, 1996

§ 102(e) Date: Sep. 20, 1996

[87] PCT Pub. No.: WO95/25964

PCT Pub. Date: Sep. 28, 1995

[30] Foreign Application Priority Data

Mar. 21, 1994 [SI] Slovenia ............... P-9400141

[51] Int. Cl.$^6$ ............... B02C 19/12
[52] U.S. Cl. ............... 241/21; 241/27; 241/33; 241/38
[58] Field of Search ............... 241/20, 24.14, 241/21, 27, 33, 38, 79.1

[56] References Cited

U.S. PATENT DOCUMENTS

| | | |
|---|---|---|
| 4,291,271 | 9/1981 | Lauffer . |
| 4,413,512 | 11/1983 | Zemanek, Jr. . |
| 4,828,685 | 5/1989 | Stephens ............... 241/24.14 X |
| 4,885,540 | 12/1989 | Snoddy et al. . |
| 5,096,826 | 3/1992 | Barbic et al. . |
| 5,651,505 | 7/1997 | Lidstrom ............... 241/16 |

FOREIGN PATENT DOCUMENTS 0544585  6/1993  European Pat. Off. .

OTHER PUBLICATIONS

EPEE Cement Industry Technical Conference, May 1966, Denver, Colorado, pp. 106, W. Wieland "Automatic Fineness Control".
Journal of the American Ceramic Society, vol. 72, No. 11, Nov. 1989, New York, pp. 2126–2130, S. Bhattacharja et al. Internal Structure of Porous Silica: A Model System for Characterization by Nuclear Magnetic Resonance.
Journal OF Applied Physics, vol. 59, No. 8, 15 April 1986, New York, pp. 2788–2797, E. J. Schmidt et al. Quantifying Solid–Fluid Interfacial Phenomena In Porous Rocks with Proton Nuclear Magnetic Resonance.

Primary Examiner—John M. Husar
Attorney, Agent, or Firm—Jacobson, Price, Holman & Stern, PLLC

[57] ABSTRACT

According to the method for controlling the grinding of mineral raw materials, at a predetermined value $i^*$ of the impregnation level to which the fines of the specimen are impregnated by the impregnating agent, the effective spin-lattice relaxation time of the impregnating agent protons is measured. Each time the parameters of the grinding process are set so that the approximation $s'_{NMR}$ for the specific surface area of the fines will attain a prescribed value $s°_{NMR}$. Each time the residue percentage of the fines retained on a sieve is determined and at the onset of an increase of the residue percentage the grinding is controlled so that a subsequent agglomeration of fines particles is suppressed. The fines are impregnated by a liquid impregnating agent comprising hydrogen atoms. In the appliance of the invention the measuring and control unit comprises a measuring unit consisting of a measuring vessel and a digital automatic analytical balance, which are preferably situated in vacuum tank, and a nuclear magnetic resonance spectrometer with coherent pulses. According to the proposed method the grinding control is based on a detected agglomeration of fine particles of the fines.

11 Claims, 3 Drawing Sheets

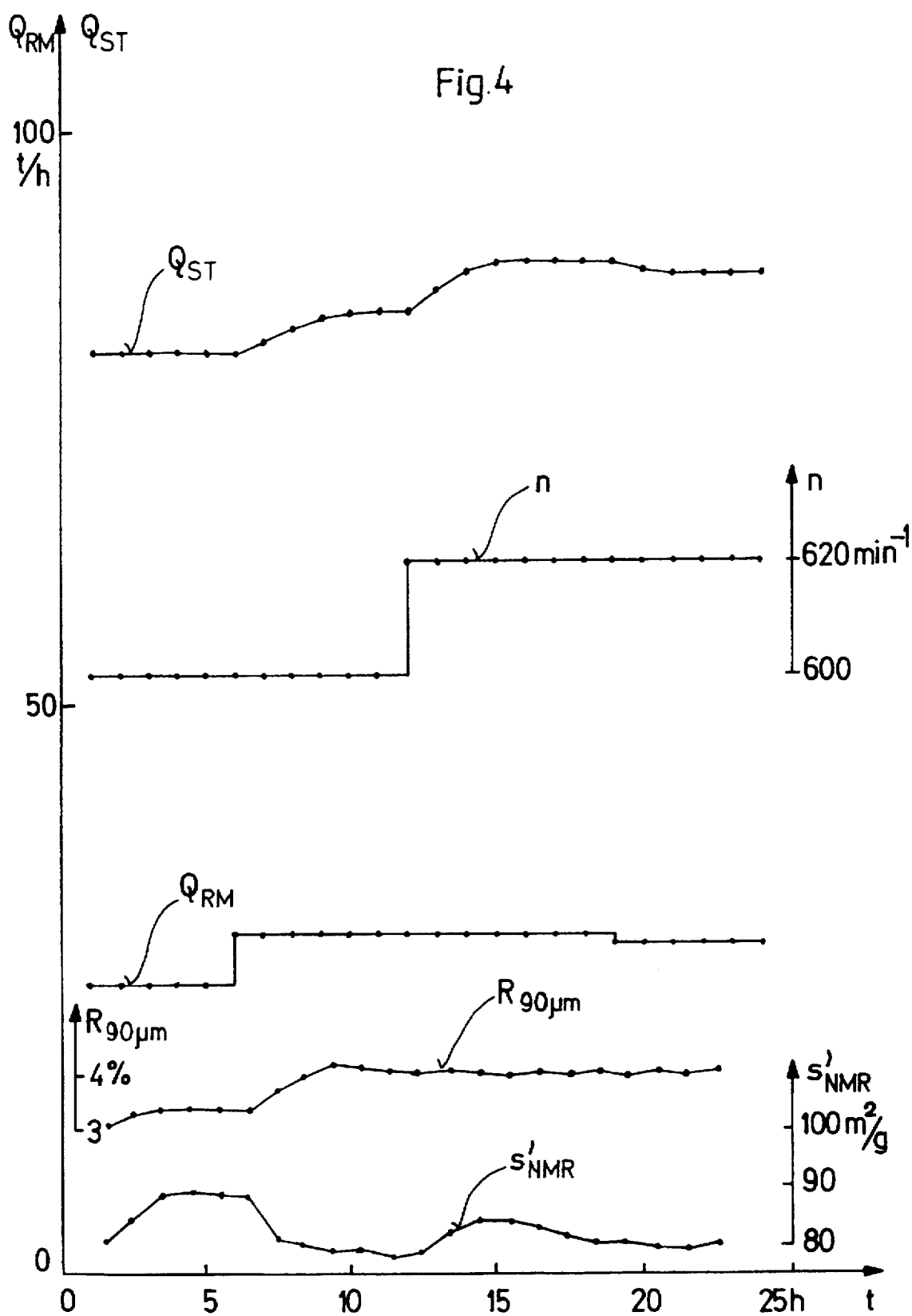

METHOD AND APPARATUS FOR CONTROLLING THE GRINDING OF MINERAL RAW MATERIALS

BACKGROUND OF THE INVENTION

The invention concerns a method for controlling the grinding of mineral raw materials, which is primarily based on a current determination of the specific surface area of the fines, and an appliance for performing said method as well as fines obtainable by such grinding.

A constant quality of fines, e.g. of cement fines, can be obtained at minimum production costs if several measured variables are watched and, correspondingly, the grinding process is controlled in an exact manner. Preferably raw material components are fed to a mill in a constant composition and by a constant mass flow. This also applies to the furnace temperature and to the temperatures of the ingredients. Tolerances are within narrow intervals. Some producers obtain products of good quality by empirically controlling the furnace and the mill on the basis of simply measurable physical quantities as e.g. at the mill on the basis of a residue percentage on a 90 µm sieve and on the basis of measuring the mill sound by an electric ear.

As a precautionary measure, cement is often ground to a higher fineness than required. However, this is an expensive measure since finish grinding requires about 38% of the total power demand of a cement plant, and this precaution can be omitted by continuously surveying the fineness of the cement fines (W. Duda, Cement Data Book, 1985 Bauverlag GmbH, Wiesbaden, Berlin, Vol. 2, pp. 76–92).

It has been proved by investigations that by refined methods higher quality products can be obtained. A surveillance of the fineness of the fines has to be a part of the control system of an automated grinding plant.

For this purpose at Holderbank, Switzerland, a Blaine permeability-meter, operating continuously and coupled to the grinding process, has been devised to determine the specific surface areas of cement (Wieland, W., Automatic Fineness Control, IEEE Cement Industry Technical Conference, May 1969, Toronto, Canada). A measurement can be carried out every 4 minutes. In an open circuit grinding plant a feed weigher is controlled by measurement results, whereas in a closed circuit grinding plant the speed of a selector drive in a separator for the separation of fine and coarse particles is controlled by the Blaine permeability-meter and the feeding of the raw material at the mill inlet is controlled by an electric ear signal and by the mass flow of the fines leaving the mill. In industrial operation the Blaine permeability-meter is exposed to clogging since fresh cement fines are more adhesive than stored cement used for measurements in a laboratory (W. Wieland, Automatic Fineness Control, IEEE Cement Industry Technical Conference, May 1966, Denver, Colo., USA).

Further there has been known a highly sophisticated mesurement system "Turbo Powsizer" of Sankyo Dengyo, Tokyo for on-line fineness control of cement fines (Powder Handling & Processing, 4 (1), 9–22 (1992)). Cement fines are automatically sampled from a production separator and after weighing, weight being memorized, the fines are fed to a turboclassifier. The turboclassifier is set to a speed that matches the desired dimension limit of the fines particles. The coarse material from the turboclassifier is weighed again and the ratio of coarse material mass to sample mass is converted into the Blaine specific surface area of the fines leaving the production separator. The speed of the production separator is controlled so that the prescribed Blaine specific surface area is obtained from the measuring system. By the turboclassifier, of course, also fine cement particles agglomerated to clumps of right dimension are separated out.

U. Haese cites various particle size distribution analyzers for the determination of the distribution of the fines particle size (U. Haese, Powder Processing Machinery and Equipment in Japan, Powder Handling & Processing, 4 (1), 9–22 (1992)): light scattering analyzers, Fraunhofer diffraction analyzers, analyzers based on light extinction by a homogeneous fines suspension during a liquid phase sedimentation, analyzers based on measurement of the transition time of a constantly scanning laser beam on individual particles, analyzers based on the time of flight of particles and fully automated sieving devices. Some of the said analyzers are applicable to on-line measurements currently surveying the fines.

It is evident on physical grounds that by none of the cited analyzers and methods to control the grinding of mineral raw materials numerous very tiny particles sticking to each other or clinging to the surface of larger particles can be detected. Therefore the agglomeration of fines particles is not detected thereby. The detection of the agglomeration, however, is very important also in order to save the grinding work and to reduce the risk of mill clogging. Additionally, the particle size data give no evidence on the micro-cracks of the particle surface.

Certainly the data of the Blaine specific surface area furnished to the purchaser are related to the strength of the obtained concrete. By the Blaine method, however, the total particle surface area wetted by water when using cement is not encompassed. Therefore the Blaine method does not provide the actual specific surface of the fines. Hence the grinding product is not designated by a physical quantity which e.g. for cement determines its later bonding capacity or for other ground mineral materials determines their degree of improvement. According to the state of art there still exists the relevant question which parameter at the grinding of mineral raw materials is most closely connected to the concrete strength or to the degree of the raw material improvement.

In general, the denser is a concrete obtained from a standard cement, the higher are its strength, and its resistance against corrosion and frost, the lower is its permeability and so forth. A denser concrete is obtained by a more densely packed cement. Therefore, in some cement plants according to local possibilities the density of the microscopic package of cement is increased by admixing a filler, e.g. several weight percents of silica fume, granules of which have a diameter of approximately 0.2 µm, or several weight percents of pure limestone (more than 95% $CaCO_3$) or other admixtures, which requires high expenditure. There have to be provided, e.g. high-quality silica fume as well as a closed internal transport of the silica fume, silica fume silos, additional feed weighers etc. In the literature the silica fume is explained mainly to fill the space among the particles of the cement stone and to establish a denser structure of concrete (A. Kumar and Della M. Roy, A Study of Silica-Fume-Modified Cements of Varied Fineness, J. Am. Ceram. Soc., 67 (1984), 61–64). Within concrete the silica fume, however, is a foreign matter and its content has to be below 15%. Otherwise the resistance of concrete against frost is adversely influenced since within concrete additional space has to be provided for ice. Anyhow, the quality of cement fines is also determined by the distribution of the dimensions of fines particles in the sub-micrometer region. In this region granulometry does not provide appropriate means to control the grinding intended to obtain fines which would contain agglomerated tiny particles of fines, yet at an agglomeration degree still tolerated by the grinding process.

SUMMARY OF THE INVENTION

Consequently, the technical problem to be solved by the present invention is how to provide such a method and to construct such an appliance (also referred to herein as an apparatus) for controlling the grinding of mineral raw materials that the grinding of a mineral raw material will actually proceed until the real specific surface area of fines has acquired a predetermined value, i.e. the agglomeration of the finest fines particles having a large active surface will be currently detected and either the agglomeration will be watched in order to raise the capacity of the grinding unit at a still allowable agglomeration or the agglomeration will be prevented by an appropriate control of the grinding process and that, consequently, all method steps will be able to be performed fast with respect to the course of the grinding process.

At the embodiment of the method for controlling the grinding of mineral raw materials according to the invention this is accomplished in that by a nuclear magnetic resonance spectrometer with coherent pulses for a specimen of fines, which are taken from the fines outlet of the grinding unit and are uniformly impregnated by an impregnating agent, the effective spin-lattice relaxation time $T_{1\ ef}(i^*)$ of the impregnating agent protons is measured at a predetermined value $i^*$ of the impregnation level $i=m_j/m$ to which the fines are impregnated by the impregnating agent, $m_j$ meaning the impregnating agent mass and m meaning the mass of the fines within the specimen (P), and that the value of the approximation $$s'_{NMR} = A \cdot T_{1b} \cdot [T^{-1}_{1\ ef}(i^*)/i^{*-1}]$$

for the specific surface area of the fines as determined by means of the nuclear magnetic resonance is calculated, where A is the surface area covered by the molecules comprised in 1 g of the impregnating agent and $T_{1b}$ is a relaxation time value that the effective relaxation time $T_{1\ ef}$ approaches when the impregnating agent has been removed for a long time, both A nad $T_{1b}$ depending only on the impregnating agent and on the fines material, and in that a residue percentage of coarse fraction portions of the fines is determined and in that at the onset of an increase of the residue percentage of coarse fraction portions of the fines the grinding is controlled so that the further agglomeration of fines particles is suppressed and in that according to the instantaneous value of the said approximation $s'_{NMR}$ the parameters of the grinding unit are set so that the approximative specific surface area $s'_{NMR}$ for the fines will attain a prescribed value $s^o_{NMR}$.

According to the first variant of the embodiment of the invention the residue percentage of coarse fraction portion of the fines is determined as the residue percentage $R_d$ of the fines retained on a sieve with appropriate openings with a width d.

According to the second variant of the embodiment of the invention the residue percentage of coarse fraction portions of the fines is determined by a granulometry.

According to the invention specimen of fines impregnated by an impregnating agent at an impregnation level i is prepared, which value may exceed the predetermined value $i^*$, and the impregnating agent is removed from the specimen by evaporation at a pressure below the saturated vapour presure of the impregnating agent for the specimen temperature, until the predetermined value $i^*$ of the impregnation level i is reached.

According to a preferred embodiment a constant temperature of the specimen is provided for. The fines are impregnated by a liquid impregnating agent comprising hydrogen atoms, e.g. water. Preferably, water is removed from a cement specimen until the predetermined value $i^*\approx0.15$ of the impregnation level i has been reached.

At the embodiment of the appliance for controlling the grinding of mineral raw materials according to the invention this is accomplished in that an uncovered measuring vessel for the specimen is fastened to a scale of a digital automatic analytical balance, the lower end of the vessel being surrounded by a coil and situated between the pole pieces of a nuclear magnetic resonance spectrometer with coherent pulses, and that to the input of a computer a first signal representing the impregnation level i from the output of the digital automatic analytical balance and a second signal representing the effective spin-lattice relaxation time $T_1$ $_{ef}(i^*)$ of the impregnating agent protons from the output of the nuclear magnetic resonance spectrometer are conducted and in that at the output of the computer each time when the impregnation level i of the specimen of the impregnated fines reaches the value $i^*$ a third signal $s'_{NMR}$ appears, which represents the product of the values A and $T_{1b}$. A representing the surface area covered by the molecules comprised in 1 g of the impregnating agent and $T_{1b}$ representing the value which the relaxation time $T_1$ $_{ef}$ approaches at continuing evaporation, and of the quotient of the reciprocal value of the effective spin-lattice relaxation time $T_1$ $_{ef}(i^*)$ of the impregnating agent protons within the specimen (P) and of the reciprocal value of the impregnation level $i^*$ and in that the third signal $s'_{NMR}$ is conducted to another computer, whereto also signals related to parameters of the grinding unit and to the residue percentage $R_d$ of the fines retained on a sieve are conducted, and signals to control the grinding unit are tapped at the output of this computer.

According to a preferred embodiment the third signal $s'_{NMR}$ represents the quotient $D_{NMR}$ being equal to the said product divided by A and $T_{1b}$.

The measuring vessel is detachably fastened to the scale of a digital automatic analytical balance. The digital automatic analytical balance and the measuring vessel may be situated within a vacuum tank.

And finally the fines of the invention are characterized as obtainable by the above method for controlling the grinding of mineral raw materials in the region of the primary or excesssive agglomeration.

The method and the appliance of the invention make possible such current control of grinding a mineral raw material that the fines at the outlet of a grinding plant will be characterized by their specific surface area $s'_{NMR}$ as determined by nuclear magnetic resonance according to a simplified method adjusted to fresh fines and, of course, by the proposed method, therefore the fines will be characterized principally by their actual fineness including the surface area of outward pores on the surface of fines particles, the actual fines fineness being a physical quantity which is relevant to the use of fines. The actual fines fineness e.g. at the cement is most intimately related to the compression strength of the concrete produced therefrom.

Another advantage of the method and of the appliance of the invention exists in that they make it possible to currently detect the agglomeration of very tiny particles of fines whereafter the agglomeration is either watched in order to increase capacity of grinding plant at a still tolerated agglomeration degree or the agglomeration is suppressed immediately by appropriately controlling grinding process, whereby the fines fraction of too fine particles disappears, which e.g. at cement later favourably influences the quality of concrete.

DESCRIPTION OF THE DRAWINGS

The invention will now be described by way of example and with reference to the accompanying drawings representing in.

DESCRIPTION OF THE PREFERRED EMBODIMENTS

The method of the invention for controlling the grinding of mineral raw materials is based on a current determination of an approximation $s'_{NMR}$ of the specific surface area as determined by the nuclear magnetic resonance and, according to a preferred embodiment of the invention, it is based on a current determination of the residue percentage $R_d$ of fines retained on a d µm sieve and, according to another preferred embodiment of the invention, it is based on a current determination of the fines granulometry.

In the case of a closed circuit grinding plant, samples S of fines are taken at the separator outlet (FIG. 3) and in the case of an open circuit grinding plant, samples S of fines are taken at the mill outlet at predetermined moments of the grinding process which are preferably equidistant in time, e.g. for a time interval of the order of 10 minutes. In dosing devices 1 and 2 a mass m of the fines and a mass $m_i$ of the impregnating agent, respectively, are dosed and in a mortar 3 they are carefully mixed and kneaded for several minutes so that agglomerated particles get wetted, they need not, however, get entirely dissolved. A specimen P prepared in such a manner is put into a measuring vessel 41. The specimen P made of the impregnated fines has an impregnation level $i=m_i/m$ exceeding the predetermined value $i^*$. Preferably the impregnating agent is removed from the specimen P by evaporation in a vacuum system at a pressure below the saturated vapour pressure of the impregnating agent for the specimen temperature until the predetermined impregnation level value $i^*$ has been reached and, currently, the effective spin-lattice relaxation time $T_{1\,ef}(i^*)$ of the impregnating agent protons in the specimen P and the impregnation level i are measured. Preferably, the temperature of the specimen P is constant during the measurement.

Figure 1:
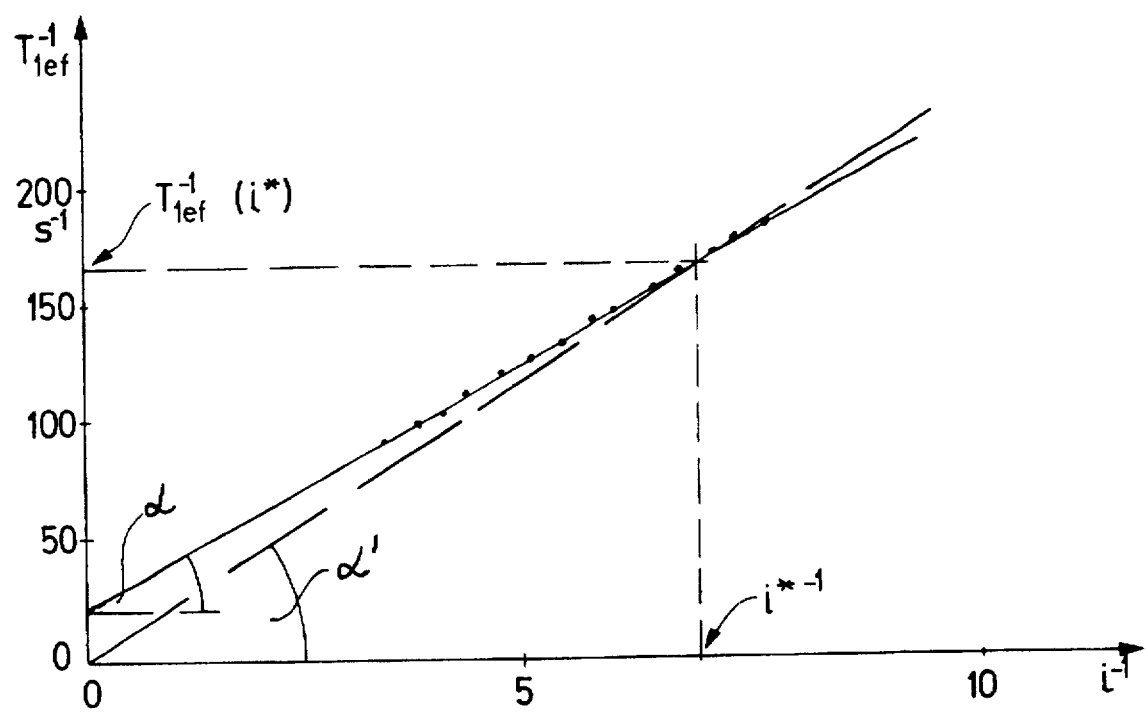
FIG. 1 a graph presenting values of the reciprocal effective relaxation time $T_{1\,ef}$ of impregnating agent protons vs. values of the reciprocal impregnation level i for a specimen made of fresh and still warm cement fines impregnated with water and produced in an industrial grinding plant at a particular moment of a grinding process, FIG. 2 a graph presenting an approximation $s'_{NMR}$ of the specific surface area as determined by the nuclear magnetic resonance, the residue percentage $R_{90\,\mu m}$ of fines retained on a 90 µm sieve and the Blaine specific surface area $s_{Blaine}$ of the cement fines vs. time during a grinding process, FIG. 3 a schematic presentation of an appliance for performing the method for controlling the grinding of mineral raw materials together with a closed circuit grinding plant, FIG. 4 a graph presenting, for cement fines, the time dependence of the approximation $s'_{NMR}$ of the specific surface area, of the residue percentage $R_{90\,\mu m}$ of fines retained on a 90 µm sieve, of the mass flow $Q_{RM}$ of fed raw material, of the rotation speed n of a separator selector and of the mass flow $Q_{ST}$ of separator tailings back to the mill in a closed circuit grinding plant.

In FIG. 1 a graph representing the reciprocal values of the effective relaxation time $T_{1\,ef}$ of impregnating agent protons in the specimen P versus reciprocal values of each corresponding impregnation level i is shown. The specimen P is made of fresh and still warm fines impregnated by water. The fines are produced in an industrial grinding plant at a particular moment of the grinding process. The effective spin-lattice relaxation time $T_{1\,ef}(i^*)$ of the impregnating agent protons is measured just when the fines in the specimen P are homogeneously impregnated to reach the predetermined value $i^*$ of the impregnation level i. Then the above mentioned approximation for the specific surface area as proposed within the scope of the invention is evaluated as follows:

$$s'_{NMR}=A\cdot T_{1b}\cdot[T^{-1}_{1\,ef}(i^*)/i^{*-1}];$$

here A is the surface area covered by the molecules comprised in 1 g of the impregnating agent and $T_{1b}$ is the relaxation time value, which the effective relaxation time $T_{1\,ef}$ approaches when the impregnating agent has been removed for a long time (see below). A and $T_{1b}$ only depend on the kind of the impregnating agent and on the fines material. For water as the impregnating agent, A is equal to $3.82 \cdot 10^3$ m²/g.

There has been known a method for determining the specific surface area $s_{NMR}$ of a porous or a powdery substance by means of nuclear magnetic resonance (patent YU 46.092 and its patent family consisting of patents U.S. Pat. No. 5,096,826, DE 38 39 290, CH 678 112 and of a patent granted on the patent application SU 4 356.971.25). A substance, whose specific surface area $s_{NMR}$ has to be determined—in the present case the fines—is impregnated by an impregnating agent that comprises hydrogen atoms and does not react chemically with the examined substance nor gets occluded by it. A sample of the examined substance is impregnated by a determined mass of the impregnating agent mass to get a specimen of the required impregnation level i. The impregnating agent is removed by evaporation in vacuum and at every interruption of the removal the impregnation level i of the specimen is determined by weighing and, by means of a NMR spectrometer applying coherent pulses, the effective relaxation time $T_{1\,ef}$ of the impregnating agent protons in the specimen corresponding to the impregnation level i is measured. Some impregnating agent molecules are adsorbed on the surface of the examined substance, other molecules, however, are not influenced by said substance and they behave like in a specimen of the pure impregnating agent. Because of the interchange of the impregnating agent molecules the effective relaxation time $T_{1\,ef}$ is measured, which depends on the relative number of the impregnating agent molecules within each mentioned phase. From the graph representing the reciprocal effective relaxation time $T_{1\,ef}$ versus the reciprocal impregnation level i, the slope $\Delta T_{-11\,ef}/\Delta(m_i/m)^{-1}$ of the straight line and the ordinate section representing the reciprocal value of the relaxation time $T_{1a}$ for the impregnating agent in situ are determined. Thereafter, at a reduced impregnation level i of the specimen after a long uninterrupted removal of the impregnating agent, also the relaxation time $T_{1b}$ of the protons in the impregnating agent molecules, which in a monomolecular layer remained adsorbed to the pore walls, is measured as a limit or the lowest value towards which finally the effective relaxation time $T_{1\,ef}$ tends during the removal of the impregnating agent. The specific surface area $s_{NMR}$ as determined by means of the nuclear magnetic resonance is finally evaluated from the following expression:

$s_{NMR}=A\cdot(1/T_{1b}-1/T_{1a})^{-1}\cdot[\Delta(1/T_{1ef})/\Delta i^{-1}]$.

In FIG. 1 a visual comparison of the exact expression $s_{NMR}$ for the specific surface area with the approximative expression $s'_{NMR}$ as proposed within the method of the invention is given. Pleasuring results for different values of the impregnation level i of fines sampled as one single sample S at a particular moment of the grinding process at the outlet of the grinding plant are situated in the presented graph on a straight line with an inclination angle α. In the expression for the specific surface area, $s_{NMR}$ is determined by tg $\alpha=\Delta(1/T_{1ef})/\Delta i^{-1}$. In the approximative expression for the specific surface area, however, $s'_{NMR}$ is represented by $[T^{-1}_{1ef}(i^*)/i^{*-1}]$=tg α', where α' is the inclination angle of the straight line through teh origin of the coordinate system and through a point on this straight line corresponding to the reciprocal value $i^{o-1}$ of the impregnation level. The value i* of the impregnation level should preferably be lower than 0.20 so that tg α and tg α' differ only slightly. In the approximation $s'_{NMR}$ the value of $1/T_{1a}$ is neglected with respect to $1/T_{1b}$ (L. Barbič et al., J. Am. Ceram. Soc., 65 (1982), 25–31; S. Bhattacharja et al., J. Am. Ceram. Soc., 72 (1989), 2126–30). The described differences appear also owing to the properties of fresh fines as it will be explained below.

Obviously tg α can be determined for each fines sample by measuring the effective relaxation time $T_{1ef}$ at several values of the impregnation level i. To control the grinding process it actually suffices to watch the time dependence of the approximation $s'_{NMR}$ for specific surface area of the fines or even of the factor $D_{NMR}=T^{-1}_{1ef}(i^*)/i^{o-1}$ in the approximation $s'_{NMR}$ for the specific surface area since the relaxation time $T_{1b}$ of the protons in the molecules of the impregnating agent, which remained adsorbed to the pore surface of the fines particles, does not depend on the fineness of the fines. Thus, at different moments of the grinding process the relaxation time $T_{1b}$ of the protons is the same for the same material and can be determined in each grinding process once and for all if the composition of ingredients is constant.

The parameters of the grinding process are set so that the approximation $s'_{NMR}$ for the specific surface area of the fines which as a final product leave the grinding plant, has a prescribed value $s^o_{NMR}$.

At those particular moments of the grinding process when the fines samples S are sampled for the determination of the approximation $s'_{NMR}$ of the specific surface area of the fines, preferably simultaneously also a residue percentage $R_d$ of the fines retained on a sieve with appropriate openings with a width d is measured or/and a granulometry according to any known method, e.g. by the laser granulometric method, is determined. If the value of the residue percentage $R_d$ of the fines retained on the sieve starts to grow or the granulometry starts to change correspondingly at a simultaneous growth of the value of the approximation $s'_{NMR}$, the grinding process is adjusted so as to suppress further agglomeration of the fines particles.

Figure 2:
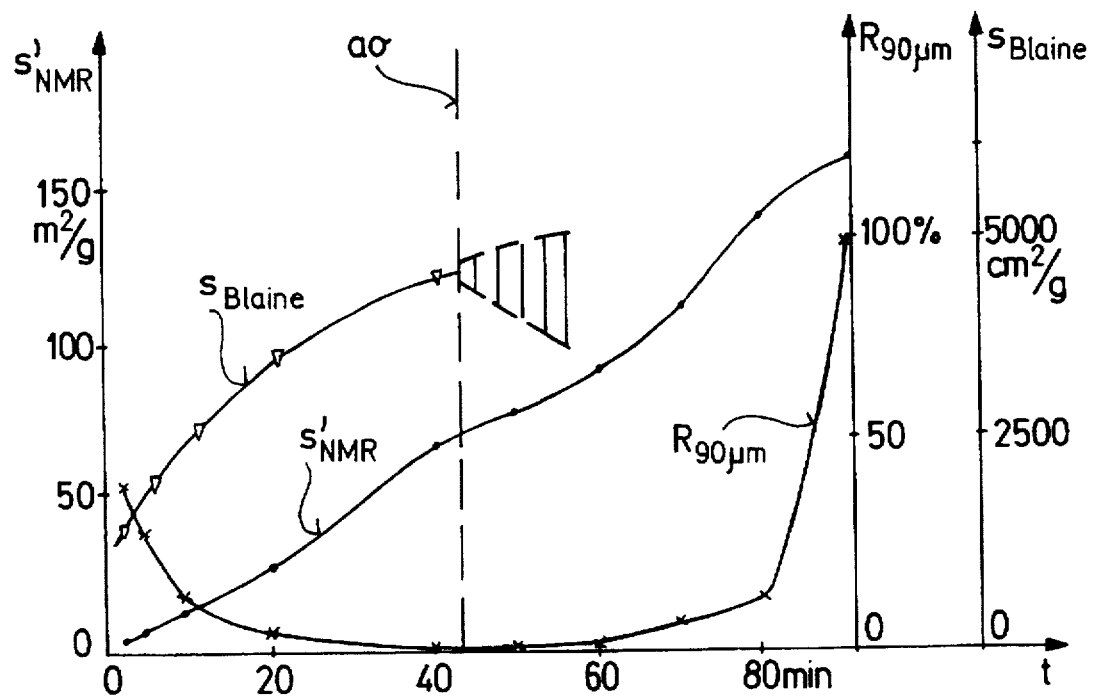

The basic idea of the current determination of the residue percentage $R_d$ of the fines retained on a sieve and of the specific surface area $s'_{NMR}$ is clearly illustrated by the graph in FIG. 2 representing the approximation $s'_{NMR}$, the residue percentage $R_{90\ \mu m}$ of the fines retained on a 90 μm sieve and the Blaine specific surface area $s_{Blaine}$ for the fines consisting of 95 g of clinker and of 5 g of dry gypsum versus the time of grinding in a ball mill with the diameter of 97 mm and with three steel balls having a mass of 200 g each and the diameter of 29.5 mm at 225 revolutions per minute. At the beginning the residue percentage $R_{90\ \mu m}$ of the fines retained on the 90 μm sieve drops since the dimension of the fines particles decreases, whereafter the residue percentage $R_{90\ \mu m}$ gets stationary near the moment oa when the primary agglomeration of the fines particles sets on. Then the residue percentage $R_{90\ \mu m}$ starts to grow and after 80 minutes of grinding it rises steeply since clumps of clogged material appear. All the time of the grinding, however, the value of the approximation $s'_{NMR}$ for the specific surface area increases since at the determination thereof the impregnating agent after thorough kneading of the cement paste wetted by water makes also the finest particles wet, the dimension of which particles is reduced all the time of the grinding irrespective of agglomerating of a part of fines particles. The approximation $s'_{NMR}$ for the specific surface area is therefore a reliable measure for the actual fineness; it also encompasses the surface area of outwards open pores on the surface of the fines particles and hence it presents a real specific surface area of the fines particles. The Blaine specific surface area increases up to the moment oa when the primary agglomeration of the fines particles sets on, thereafter its time development, however, is not stable; it may further grow or it may start to drop. The described example shows that the current watching of the approximation $s'_{NMR}$ and of the residue percentage $R_{90\ \mu m}$ of the fines retained on e.g. a 90 μm sieve makes possible to find out the onset of agglomeration whereas the Blaine method does not furnish reliable values for the specific surface of the fines anymore. Therefore the fines produced in the grinding process controlled by the method of the invention have new properties determined by the two parameters $s'_{NMR}$ and $R_{90\ \mu m}$ and by the grinding process itself as controlled according to the method proposed by the invention.

According to the method of the invention, liquid impregnants comprising hydrogen atoms like $H_2O$, $C_2H_5OH$, $C_6H_{12}$ and similar ones are used to impregnate fines. To control the cement grinding process preferably water is used as the impregnating agent; in this case the specimen P is left to dry at least to the predetermined value $i^*\approx0.15$ of the impregnation level i and at this value i* of the impregnation level the value $T_{1ef}(i^*)$ of the effective relaxation time is determined. The value $i^*\approx0.15$ is appropriate for cement fines impregnated by water since under this condition a swift diffusion exchange of water molecules adhering to the surface of the cement fines particles with other water molecules in the specimen P is made possible.

Due to a rather strong NMR signal and a short spin-lattice relaxation time as well as due to a weak evaporation at atmospheric conditions, water is preferably used as the impregnating agent. The hydratation of fresh and still warm cement—the temperature of the samples S of fresh fines varies with grinding conditions and can approach or exceed 100° C.—affects the reproducibility of the initial relaxation rate $1/T_{1a}$ which is relatively weak. At several fresh cements there additionally appears a non-exponential character of the longitudinal relaxation function, whereto the effective relaxation time $T_{1ef}$ is related. Then the effective relaxation time $T_{1ef}$ is determined by means of averaging, which does not spoil the linear dependence represented in FIG. 1.

Figure 3:
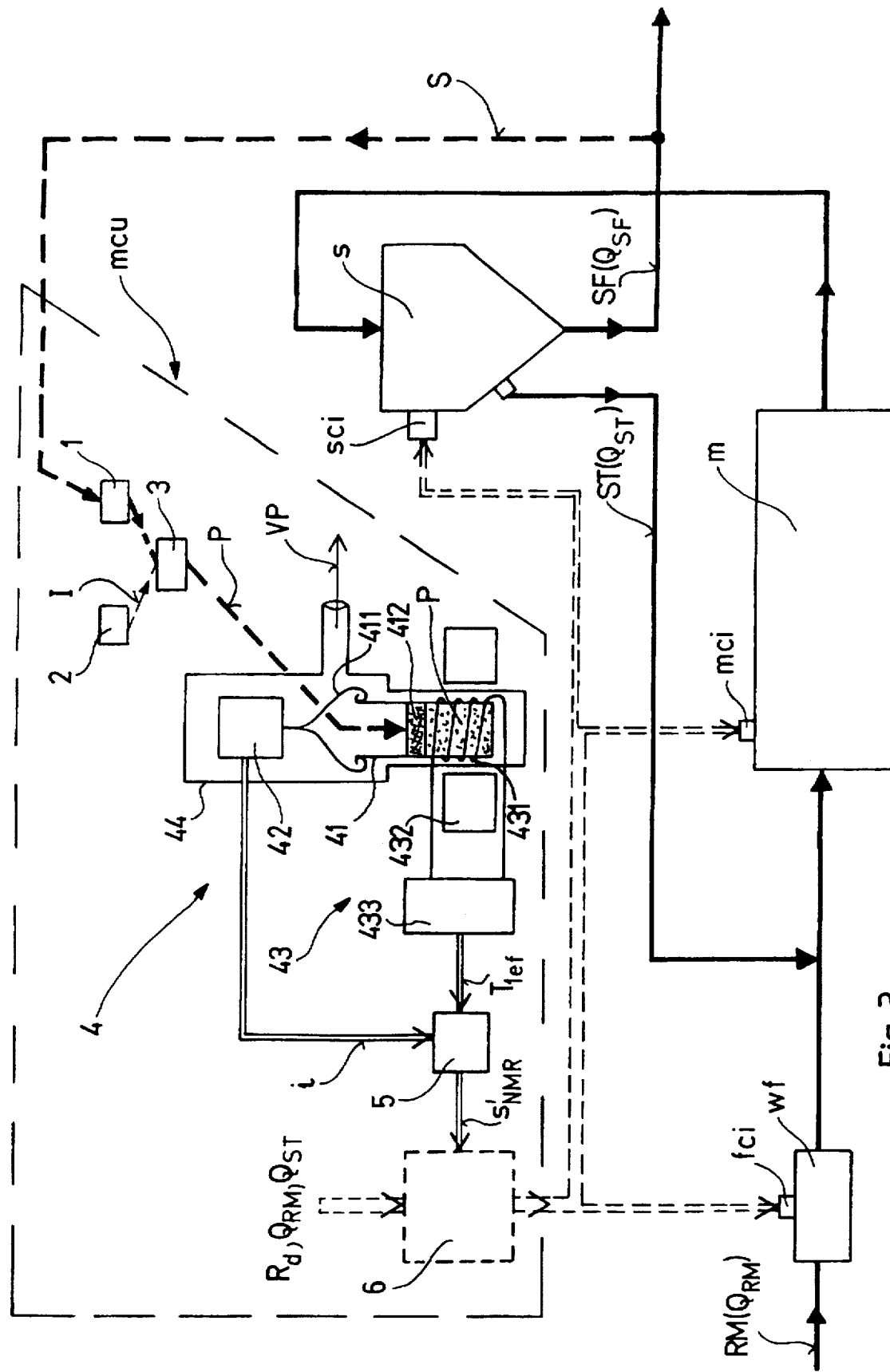

The apppliance according to the invention to perform the method for controlling the grinding of mineral raw materials comprises—in addition to accessories like dosing devices 1 and 2 for the fines and the impregnating agent, respectively, a mortar 3 and a sieve with appropriate openings with a width d (not shown)—a measuring and control unit mcu (FIG. 3). The measuring and control unit mcu comprises a measuring unit 4 and a computer, which for reasons of clarity will be treated as two computers 5 and 6. The measuring unit 4 comprises a measuring vessel 41, a digital automatic analytical balance 42 and a nuclear magnetic resonance spectrometer 43 with coherent pulses.

The requirements of the method according to the invention are met by a nuclear magnetic resonance spectrometer with coherent pulses at which the total duration of a π/2-pulse and of a dead time exceeds 10 μs.

The uncovered measuring vessel 41 for the specimen P, which therein may be covered by a permeable cover 412, is detachably fastened by means of a fixture 411 to the scale of a digital automatic analytical balance 42. Preferably, the balance 42 and the measuring vessel 41 are placed into a vacuum tank 44, which is connected to a vacuum pump (marked by an arrow VP). Since the measuring vessel 41 is entirely in vacuum, no moisture appears on its outer walls which would disturb the determining of the impregnation level i of the sample P. The lower end of the vessel 41, where the sample S is placed, is surrounded by a coil 431 connected to a circuit 433 of the NMR spectrometer 43 and is situated between the spectrometer pole pieces 432.

To the input of the computer 5 there are conducted on the one hand a signal representing the impregnation level i of the sample S from the output of the digital automatic analytical balance 42 and on the other hand a signal representing the effective spin-lattice relaxation time $T_{1\ ef}$ of the impregnating agent protons from the output of the circuit 433 of the NMR spectrometer 43. Into the computer 5 also data pertaining to the impregnating agent and to the material being ground are conducted: a surface area A representing the surface covered by the molecules comprised in 1 g of the impregnating agent and the value $T_{1b}$, which the relaxation time $T_{1\ ef}$ of the impregnating agent protons in the sample S approaches at continuing evaporation. Each time when the impregnation level i of the specimen P reaches the value i*, at the output of the computer 5 there appear either a signal $s'_{NMR}$ representing a product of the value s A and $T_{1b}$ and of a factor $D_{NMR}$ being the quotient of the reciprocal value of the effective spin-lattice relaxation time $T_1\ _{ef}(i*)$ of the impregnating agent protons within the specimen P and of the reciprocal value of the impregnation level i* or simply the said factor $D_{NMR}$ according to the variant embodiment of the invention.

The grinding process is controlled so that the value of the approximation $s'_{NMR}$ for the specific surface area of the fines and the value $R_d$ of the residue percentage of the fines retained on a sieve are situated within the tolerance interval around the prescribed corresponding values $s°_{NMR}$ and $R°_d$. A manual control can be carried out on the basis of the approximation $s'_{NMR}$ value for the specific surface area calculated in the computer 5 and by taking into account the residue percentage $R_d$ on the sieve and, of course, by taking into account e.g. for the closed circuit grinding unit in FIG. 3, the following parameters, which, however, are set afterwards during the controlling of the process: the mass flow $Q_{RM}$ of the raw material RM, the air vent m, the feeding of additives during the grinding process the speed n of selector rotation, the inclination and the number of selector vanes in the separator s, whereby the mass flow $Q_{SF}$ of the fines and the mass flow $Q_{ST}$ of the separator tailings are influenced.

Obviously, the signal $s'_{NMR}$ from the output of the computer 5 can be conducted to the computer 6, whereto also signals related to relevant parameters of the grinding unit and preferably also the value of the residue percentage $R_d$ of the fines retained on a sieve are conducted. The signals to control the grinding are tapped at the output of the computer 6 and in the case of the closed circuit grinding plant, are conducted to the following control inputs: an input fci of the dosing weigher, an input mci symbolically, representing the inputs to set the air vent m, the dosing of additives etc. and a separator input sci for setting the speed n of the selector rotation.

In the continuation an example of grinding the cement PC 30 dz 45 S in a closed circuit grinding plant is represented. The raw material also included a water-impregnated tuff. Actually, the grinding process was controlled in a known way by means of the currently determined specific surface area $s_{Blaine}$ and the residue percentage $R_{90\ \mu m}$ of the fines on the sieve, the grinding process, however, was also watched by a simultaneous determination of the fines factor $D_{NMR}$. The following table represents the mentioned physical quantities determined every hour during the grinding process right before a standstill due to a clogging of the mill occured.

| $S_{Blaine}$ | $R_{90\ \mu m}$ | $D_{NMR}$ | $Q_{RM}$ | $Q_{ST}$ | L |
|---|---|---|---|---|---|
| 4270 cm²/g | 1.2% | 17 s⁻¹ | 73 t/h | 40 t/h | 0.55 |
| 4140 | 0.7 | 20 | 73 | 45 | 0.62 |
| 4070 | 1.4 | 25 | 73 | 50 | 0.68 |
| 4050 | 1.4 | 27 | 81 | 70 | 0.86 |
| 3840 | 0.9 | 28 | 81 | 100 | 1.23 |

Strictly speaking, the specific surface area $s_{Blaine}$ was dropping slightly, yet on the contrary, rather low residue percentages $R_{90\ \mu m}$ on the sieve gave evidence of a high fineness of the cement fines. In a quantitative way this was only proved by the steeply growing factor $D_{NMR}$, whose tolerance interval [17 s⁻¹, 23 s⁻¹] for the described grinding process was considerably exceeded. Consequently an agglomeration of very fine particles of the cement fines set on. Adhesive agglomerated clumps stuck coarser particles together which resulted in the clogging of the chute for the separator tailings. Prior thereto the circulating load L and thereby also the separator tailings mass flow $Q_{ST}$ were growing steeply, whereas the mass flow $Q_{RM}$ of the raw material RM was steadily high.

There will be presented still another example of an industrial fairly steady grinding of a hydraulic binder, commercially designated "maltit z aerantom", in a closed circuit grinding plant. The grinding process was controlled according to the method of the invention by a current determination of the specific surface area $s'_{NMR}$ of the fines and of the fines residue percentage $R_{90\ \mu m}$ on the sieve (FIG. 4). At the raw material mass flow $Q_{RM}$ equal to 26 t/h and at the speed n of the separator selector rotation equal to 600 min⁻¹, the separator tailings mass flow $Q_{ST}$ was 81 t/h. Over a period of some hours the specific surface area $s'_{NMR}$ of the fines grew from 80.2 m²/g to 87.9 m²/g and also the fines residue percentage $R_{90\ \mu m}$ on the sieve grew from 3.1% to 3.5%; an excessive agglomeration set on. Therefore the raw material mass flow $Q_{RM}$ was raised to 30 t/h. The specific surface area $s'_{NMR}$ dropped to 78.7 m²/g at the fines residue percentage $R_{90\ \mu m}$ on the sieve equal to 4%. The separator tailings mass flow $Q_{ST}$ got stabilized at 84 t/h. Immediately after raising the selector speed n of rotation to 620 min⁻¹ the specific surface area $s'_{NMR}$ increased for 2 hours up to 84 m²/g, whereafter after a few hours it got stabilized at 81.4 m²/g at the fines residue percentage $R_{90\ \mu m}$ on the sieve being rather constantly at 4% and at the separator tailings mass flow $Q_{ST}$ being 88 t/h. After lowering the raw material mass flow $Q_{RM}$ to 29 t/h, the specific surface area $s'_{NMR}$ got stabilized at 80.2 m²/g at the fines residue percentage $R_{90\ \mu m}$ on the sieve equal to 4% and at the separator tailings mass flow $Q_{ST}$ equal to 87 t/h.

In the closed circuit grinding plant a separator classifying selectivity $E_{NMR}$ is simply expressed in terms of factors $D_{NMR}^{SF}(\equiv D_{NMR})$, $D_{NMR}^{ST}$ for the separator fines SF and for the separator tailings ST, respectively, as follows:

$$E_{NMR}=(1+L \cdot D_{NMR}{}^{ST}/D_{NMR}{}^{SF})^{-1},$$

wherein $L=Q_{ST}/Q_{SF}$ is a circulating load; the expression for the separator classifying selectivity $E_{NMR}$ does not depend on the limit value relaxation time $T_{1b}$. The separator classifying selectivity $E_{NMR}$ drops if the circulating load L is raised. Namely a higher separator tailings mass flow $Q_{ST}$ means that a bigger surface area of the particles is returned back to the mill and that therefore a smaller surface area of the particles is carried out of the mill. This means that the finer fraction is ground again and again, which can lead to an agglomeration of fine particles. Thus the minimum degree of agglomeration is achieved by an optimization of the separator classifying selectivity $E_{NMR}$.

By means of the method and of the appliance according to the invention even the primary agglomeration, i.e. the agglomeration in its early phase, is detected very promptly and clearly. An additional advantage of the method and of the appliance according to the invention consists in currently supplying the value of the specific surface area $s'_{NMR}$, which is very relevant for any later use of the fines, since therein also the surface area of the outwards open pores on the surface of fines particles is included. Namely the outwards open pores on the surface of fines particles will also get wet when the fines are used; this affects the quality of hydraulic binders as well the degree of the raw material improvement.

So far the suppression of agglomeration of fine fines particles, e.g. by diluting the ground material by the addition of a fresh raw material or by setting the separator so that the fine fines particles are evacuated from the grinding plant as soon as possible, has always led to a reduction of the grinding plant output whereas by the method and the appliance according to the invention the output of the grinding plant is pushed to its upper limit, since the method of the invention, by taking into account also the fineness of the finest particles, which, however are incorporated in agglomerated clumps, makes possible to blur the previous sharp dividing line between the agglomeration and the crushing as two complementary processes present at any grinding.

I claim:

1. Method for controlling the grinding of mineral raw materials, wherein by a nuclear magnetic resonance spectrometer with coherent pulses for a specimen (P) of fines, which are taken from the fines outlet of a grinding unit and are uniformly impregnated by an impregnating agent, the effective spin-lattice relaxation time $T_{1\,ef}(i^*)$ of the impregnating agent protons is measured at a predetermined value $i^*$ of the impregnation level $i=m_j/m$ to which the fines are impregnated by the impregnating agent, $m_j$ meaning the impregnating agent mass and m meaning the mass of the fines within the specimen (P), the value of the approximation $$s'_{NMR}=A \cdot T_{1b} \cdot [T^{-1}_{1\,ef}(i^*)/i^{*-1}]$$

for the specific surface area of the fines as determined by means of the nuclear magnetic resonance is calculated, where A is the surface area covered by the molecules comprised in 1 g of the impregnating agent and $T_{1b}$ is a relaxation time value that the effective relaxation time $T_{1\,ef}$ approaches when the impregnating agent has been removed for a long time, both A nad $T_{1b}$ depending only on the impregnating agent and on the fines material, a residue percentage of coarse fraction portions of the fines is determined, at the onset of an increase of the residue percentage of coarse fraction portions of the fines the grinding is controlled so that the further agglomeration of fines particles is suppressed, according to the instantaneous value of the said approximation $s'_{NMR}$ the parameters of the grinding unit are set so that the approximative specific surface area $s'_{NMR}$ for the fines will attain a prescribed value $s°_{NMR}$.

2. Method as recited in claim 1, characterized in that the residue percentage of coarse fraction portions of the fines is determined as a residue percentage $R_d$ of the fines retained on a sieve with appropriate openings with a width d.

3. Method as recited in claim 2, characterized in that the specimen (P) of fines impregnated by an impregnating agent at an impregnation level i is prepared, which value exceeds the predetermined value $i^*$, and that the impregnating agent is removed from the specimen (P) by evaporation at a pressure below the saturated vapour presure of the impregnating agent for the specimen temperature, until the predetermined value $i^*$ of the impregnation level i is reached.

4. Method as recited in claim 3, characterized in that a constant temperature of the specimen (P) is provided for.

5. Method as recited in claim 4, characterized in that the fines are impregnated by a liquid impregnating agent comprising hydrogen atoms.

6. Method as recited in claim 5, characterized in that the fines are impregnated by water as the impregnating agent.

7. Method as recited in claim 6, characterized in that water is removed from a cement specimen (P) homogeneously impregnated by water until the predetermined value $i^* \approx 0.15$ of the impregnation level i is reached.

8. Method as recited in claim 1, characterized in that the residue percentage of coarse fraction portions of the fines is determined by a granulometry.

9. Apparatus for controlling the grinding of mineral raw materials comprising, an uncovered measuring vessel (41) for a specimen (P) fastened to the scale of a digital automatic analytical balance (42), the lower end of the vessel (41) being surrounded by a coil (431) and situated between the pole pieces (432) of a nuclear magnetic resonance spectrometer (43) with coherent pulses, a first computer (5) having inputs coupled to said digital automatic balance (42) and to said nuclear magnetic resonance spectrometer (43) and having an output coupled to a second computer (6), means for providing a first signal representing the impregnation level i from an output of said digital automatic analytical balance (42) to an input of said first computer (5) and means for providing a second signal representing the effective spin-lattice relaxation time $T_{1\,ef}(i^*)$ of impregnating agent protons from an output of said nuclear magnetic resonance spectrometer (43) to an input of said first computer (5), means for providing a third signal at the output of the first computer (5) each time the impregnation level i of the specimen (P) of impregnated fines reaches the value $i^*$, said third signal representing the product $s'_{NMR}$ of the values A and $T_{1b}$, A representing the surface covered by the molecules comprised in 1 g of the impregnating agent and $T_{1b}$ representing the value which the relaxation time $T_{1ef}$ approaches at continuing evaporation, and of the quotient $D_{NMR}$ of the reciprocal value of the effective spin-lattice relaxation time $T_{1ef}(i^*)$ of the impregnating agent protons within the specimen (P) and of the reciprocal value of the impregnation level $i^*$, or represents the latter quotient $D_{NMR}$ alone, means for providing said third signal to said second computer (6), said second computer also receiving signals related to parameters of a grinding unit and to the residue percentage $R_d$ of fines retained on a sieve said second computer (6) having an output for tapping signals to control said grinding unit.

10. The apparatus of claim 9, wherein said measuring vessel (41) is detachably fastened to said scale of said digital automatic analytical balance (42).

11. The apparatus of claim 10, wherein said digital automatic analytical balance (42) and said measuring vessel (41) are situated within a vacuum tank (44).

* * * * *